US005741916A

United States Patent [19]

O'Lenick, Jr.

[11] Patent Number: 5,741,916
[45] Date of Patent: Apr. 21, 1998

[54] MEADOWFOAM ALKANOLAMIDES

[75] Inventor: Anthony J. O'Lenick, Jr., Lilburn, Ga.

[73] Assignee: Fan Tech Ltd., Chicago, Ill.

[21] Appl. No.: 692,376

[22] Filed: Jul. 31, 1996

Related U.S. Application Data

[63] Continuation-in-part of Ser. No. 516,138, Aug. 17, 1995, Pat. No. 5,646,321.

[51] Int. Cl.$^6$ .................................................. C07C 233/00
[52] U.S. Cl. ................................. 554/66; 554/61; 554/64
[58] Field of Search .......................... 554/61, 64, 66

[56] References Cited

U.S. PATENT DOCUMENTS 2,402,530   6/1946   Bousquet ........................... 554/69

*Primary Examiner*—Gary Geist
*Assistant Examiner*—Deborah D. Carr

[57] ABSTRACT

The present invention deals with the certain novel alkanolamides which are prepared by the reaction of an alkanolamie and meadowfoam fatty, methyl ester or triglyceride. These materials are useful as cosmetic ingredients as additives to shampoo systems where outstanding liquidity, resistance to oxidation, and minimal odor variation are required.

7 Claims, No Drawings

MEADOWFOAM ALKANOLAMIDES

RELATED APPLICATIONS

This application is a continuation in part of application Ser. No. 516,138 filed Aug. 17, 1995, now U.S. Pat. No. 5,646,321.

BACKGROUND OF THE INVENTION

1. Field of the Invention

The present invention deals with the certain novel alkanolamides which are prepared by the reaction of an alkanolamine and meadowfoam fatty, methyl ester or triglyceride. These materials are useful as cosmetic ingredients where outstanding liquidity, resistance to oxidation, and minimal odor variation are required. This combination of properties make these compounds excellent candidates as additives to personal care products like shampoos where they thicken formulations and stabilize foam.

The addition of between 1 and 5% alkanolamide to a 15% aqueous solution of sodium lauryl sulfate will (a) build the viscosity of the solution and (b) result in a product which has a thicker longer lasting foam. Alkanolamides are commonly used in shampoo and other personal care formulations.

2. Description of the Art Practices

Alkanolamides perform a variety of functions including viscosity enhancement, foam stabilization, emulsification, and detergency. Chemically, alkanolamides are the reaction product of an alkanolamine and a fatty material. Fatty materials are a class of compounds which include fatty carboxylic acids, fatty methyl esters and fatty glycerides (also called oils). The source of the fatty materials include coconut, peanut, soybean, and rapeseed oils, fractionated and non-fractionated fatty methyl esters and acids of almost any carbon length.

Variation of carbon chain lengths in the fatty source has direct effect upon alkanolamide properties. While short chain fatty materials result in compounds useful as humectants and hair anti-tangle agents, products based upon 8 to 10 carbon fatty acids exhibit foam stability but contribute little as thickeners. The medium range 12 to 14 carbon fatty acids are the best foam boosters, while also showing good viscosity building properties. Lauric-myristic diethanolamides are common ingredients in formulations of high foaming products such as dish wash detergent, bubble bath, and hair shampoo. They also contribute emollient and conditioning effects upon skin and hair in many formulations. This is why the lauric myristic alkanolamides have become the workhorse of the cosmetic industry.

The use of higher molecular weight unsaturated fatty alkanolamides reduce foam and foam stabilization but give good viscosity build. The optimum performance in a formulation is often obtained when one employs blends of alkanolamides having differing carbon chain lengths. This can result in the desired properties of both materials. Oleic and linoleic alkanolamides are excellent viscosity builders at low concentration in most shampoos and are of particular interest in formulations that contain surfactants which are difficult to thicken. These higher molecular weight unsaturated products because of their unsaturation suffer from oxidative instability and interfere with the fragrance of many products.

The recent availability of meadowfoam oil, with it's 20 to 22 carbon atoms and the specific location of it's double bonds, and it's reaction to make alkanolamides results in the preparation liquid stable alkanolamides, acceptable for use in personal care applications.

None of the prior amides possess the critical meadowfoam carboxy moiety. Molecules of the current invention have the meadowfoam alkyl group in the alkanolamide.

THE INVENTION

This invention relates to a particular group of alkanolamides made from meadowfoam oil, meadowfoam methyl ester or meadowfoam fatty acid. The terms meadowfoam oil, fatty acid or methyl ester as used herein refer to a specific alkyl distribution of the groups which is are native to a plant Limnathes Alba, commonly called meadowfoam oil. Meadowfoam oil is harvested from a plant and sold commercially by The Fanning Corporation under the tradename "Fancor Meadowfoam".

The unique structure of the oil results in a liquid product with oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of the alkanolamide having the unique distribution of the meadowfoam on the other result in superior liquidity, lubricity, and outstanding oxidative stability.

The compounds of the current invention are alkanolamides derived from meadowfoam conforming to the following structure;

$$R^1-C(O)-N-(R^2)$$
$$|$$
$$R^3$$

$R^1$ is derived from meadowfoam and specifically is;
60–65% by weight —$(CH_2)_3$—CH=CH—$(CH_2)_{13}$-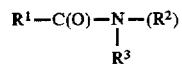
$CH_3$
12–20% by weight a mixture of
—$(CH_2)_3$—CH=CH—$(CH_2)_{15}$—$CH_3$ and
—$(CH_2)_{11}$—CH=CH—$(CH_2)_7$—$CH_3$ and
15–28% by weight
—$(CH_2)_3$—CH=CH—$(CH_2)_6$—CH=CH—$(CH_2)_6$—$CH_3$;

$R^2$ is:
—$(CH_2CH_2-O)_x$—$(CH_2CH(CH_3)O)_y$—H x, and y are independently 0 or 1 with the proviso that x+y is greater than 0.

$R^3$ is H or
—$(CH_2CH_2-O)_a$—$(CH_2CH(CH_3)O)_b$—H a, and b are independently 0 or 1 with the proviso that a+b is greater than 0.

It is also envisioned that the compounds of the present invention can be blended with lower molecular weight saturated alkanolamides which are solid at room temperature. The blended product will have improved liquidity and improved viscosity build in formulations are well as enhanced foam stabilization effects.

The invention also teaches that an alkanolamide can be made by the amidation reaction of an alkanolamine conforming to the following structure;

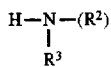

$R^2$ is:

—$(CH_2CH_2$—$O)_x$—$(CH_2CH(CH_3)O)_y$—H x, and y are independently 0 or 1 with the proviso that x+y is greater than 0.

$R^3$ is H or

—$(CH_2CH_2$—$O)_a$—$(CH_2CH(CH_3)O)_b$—H a, and b are independently 0 or 1 with the proviso that a+b is greater than 0, and meadowfoam oil.

In a preferred embodiment the amidification is conducted at a temperature of between 100° and 210° C.

PREFERRED EMBODIMENT

In a preferred embodiment x is 1, y is 0 and $R^3$ is H.

In a preferred embodiment x is 0, y is 1 and $R^3$ is H.

In a preferred embodiment x is 1, y is 0, a is 0, and b is 1.

In a preferred embodiment x is 1, y is 0, a is 1, and b is 0.

In a preferred embodiment x is 0, y is 1, a is 0, and b is 1.

In a preferred embodiment x is 0, y is 1, a is 1, and b is 0.

In a preferred embodiment the amidification is conducted at a temperature of between 100° and 210° C.

EXAMPLES

Raw Materials

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

Alkanolamines

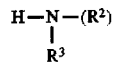

$R^2$ is:

—$(CH_2CH_2$—$O)_x$—$(CH_2CH(CH_3)O)_y$—H x, and y are independently 0 or 1 with the proviso that x+y is greater than 0.

$R^3$ is H or

—$(CH_2CH_2$—$O)_a$—$(CH_2CH(CH_3)O)_b$—H a, and b are independently 0 or 1 with the proviso that a+b is greater than 0.

Class 1 (monoalkanolamines)

Monoalkanolamines are products of commerce and are available commercially from many companies like Union Carbide. $R^3$ is H in this class of compounds.

| | | $R^2$ | |
|---|---|---|---|
| Example | | x | y |
| 1 | Monoethanolamine | 1 | 0 |
| 2 | Monoisopropanolamine | 0 | 1 |

Class 2

$R^3$ is —$(CH_2CH_2$—$O)_a$—$(CH_2CH(CH_3)O)_b$—$(CH_2CH_2$—$O)$—H

Dialkanolamines are products of commerce and are avaialable commercially from many companies like Union Carbide.

| | | $R^2$ | | $R^3$ | |
|---|---|---|---|---|---|
| Example | | x | y | a | b |
| 3 | diethanolamine | 0 | 1 | 0 | 1 |
| 4 | diisopropanolamine | 1 | 0 | 1 | 0 |
| 5 | mixed | 0 | 1 | 1 | 0 |
| 6 | mixed | 1 | 0 | 0 | 1 |

Amide Synthesis

The amidification reaction is carried out using an excess of alkanolamine or meadowfoam or more typically using an equivalent of each. The reaction can be carried out with or without catalyst.

GENERAL PROCEDURE

Meadowfoam Oil

To the specified number of grams of Alkanolamie (examples 1–6) is added then 354.0 grams of the meadowfoam oil. The temperature of the mass is raised to 150°–200° C. The amine value drops to vanishingly small levels.

The products are clear liquids and are liquid to extraordinary temperatures. They exhibit outstanding oxidative stability and do not contribute odor to personal care products. They bulid viscosity exceptionally well in shampoo systems and stabilize foam.

| | Alkanolamine | |
|---|---|---|
| Example | Example | Grams |
| 8 | 1 | 60.0 |
| 9 | 2 | 75.0 |
| 10 | 3 | 133.0 |
| 11 | 4 | 147.0 |
| 12 | 5 | 133.0 |
| 13 | 6 | 162.0 |
| 14 | 1 | 65.0 |
| 15 | 2 | 85.0 |
| 16 | 3 | 153.0 |
| 17 | 4 | 187.0 |
| 18 | 5 | 153.0 |
| 19 | 6 | 192.0 |

Liquid products which contain unsaturation are subject to an oxidation process referred to as rancidity. The double bond (conjugated or unconjugated) present for the desired liquidity is oxidized to aldehydes and ketones which react to form compounds causing bad color, and odor. In many applications including personal care applications, mal odor is a major problem, but liquidity and hydrophobicity and liquidity are desired. The presence of the aldehydic rancidity by-products produce unacceptable odor, and color and have a profound effect upon these properties at very minute concentrations. Studies have shown that the part per billion levels of some aldehydic compounds cause unacceptable properties.

RANCIDITY TESTING

Rancidity was tested using gas chromotography on the head space above the product stored at specific conditions looking for degradation products.

(Addition of 5 grams product to be tested to a 100 ml bottle equipped with a rubber septum top stored for 3 months)

| Material | Aldehyde (Head Space analysis) | Odor |
| --- | --- | --- |
| Temperature 20 C. | | |
| Example 9 | None Detected | Good |
| Example 13 | None Detected | Good |
| Example 11 | None Detected | Good |
| Unsaturated Compounds Temperature: 20 C. | | |
| Oleic acid - Guerbet 20 Ester | 80 ppm | Fair |
| Oleic Acid Guerbet 16 ester | 100 ppm | Unacceptable |
| Tridecyl Oleate | 90 ppm | Fair |
| TMP Trioleate | 120 ppm | Unacceptable |
| Temperature: 50 C. | | |
| Example 9 | None Detected | Good |
| Example 13 | None Detected | Good |
| Example 11 | None Detected | Good |
| Unsaturated Compounds | | |
| oleic acid C-20 Guerbet ester | 200 ppm | Unacceptable |
| Oleic Acid C-16 Guerbet ester | 175 ppm | Unacceptable |
| Tridecyl Oleate | 220 ppm | Unacceptable |
| TMP Trioleate | 210 ppm | Unacceptable |

I claim:

1. An alkanolamide conforming to the following structure;

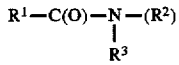

wherein:

$R^1$ is derived from meadowfoam and is;

60–65% by weight $-(CH_2)_3-CH=CH-(CH_2)_{13}-CH_3$;

12–20% by weight a mixture of
$-(CH_2)_2-CH=CH-(CH_2)_{15}-CH_3$ and
$-(CH_2)_{11}-CH=CH-(CH_2)_7-CH_3$; and 15–28% by weight
$-(CH_2)_3-CH=CH-(CH_2)_6-CH=CH-(CH_2)_6-CH_3$;

$R^2$ is:
$-(CH_2CH_2-O)_x-(CH_2CH(CH_3)O)_y-H$;

x, and y are independently 0 or 1 with the proviso that x+y is greater than 0;

$R^3$ is H or
$-(CH_2CH_2-O)_a-(CH_2CH(CH_3)O)_b-H$ a, and b are independently 0 or 1 with the proviso that a+b is greater than 0.

2. An alkanolamide of claim 1 wherein x is 1, y is 0 and $R^3$ is H.

3. An alkanolamide of claim 1 wherein x is 0, y is 1 and $R^3$ is H.

4. An alkanolamide of claim 1 wherein x is 1, y is 0 , a is 0, and b is 1.

5. An alkanolamide of claim 1 wherein x is 1, y is 0 , a is 1, and b is 0.

6. An alkanolamide of claim 1 wherein x is 0, y is 1 , a is 0, and b is 1.

7. An alkanolamide of claim 1 wherein x is 0, y is 1, a is 1, and b is 0.

* * * * *